United States Patent [19]

Chesbro et al.

[11] 4,167,450

[45] Sep. 11, 1979

[54] METHOD AND APPARATUS FOR THE PRODUCTION OF SECONDARY METABOLITES BY THE MAINTENANCE-STATE CULTIVATION OF MICROORGANISMS

[75] Inventors: William R. Chesbro, Newmarket; Robin Eifert, Durham; Thomas Evans, Dover, all of N.H.

[73] Assignee: University of New Hampshire, Durham, N.H.

[21] Appl. No.: 815,079

[22] Filed: Jul. 13, 1977

[51] Int. Cl.² ................ C12D 1/00; C12D 3/00; C12B 1/00

[52] U.S. Cl. .............................. 435/3; 435/244; 435/289; 435/311; 435/813; 435/818; 435/802

[58] Field of Search ............ 195/104, 108, 109, 115, 195/117, 139, 142, 143

[56] References Cited

U.S. PATENT DOCUMENTS

| | | | |
|---|---|---|---|
| 2,822,319 | 2/1958 | Monod | 195/115 |
| 3,015,612 | 1/1962 | Pirt et al. | 195/115 X |
| 3,252,870 | 5/1966 | Braun et al. | 195/117 X |
| 3,418,208 | 12/1968 | Coty | 195/115 X |
| 3,472,765 | 10/1969 | Budd et al. | 195/115 X |
| 3,647,632 | 3/1972 | Johnson et al. | 195/142 |
| 3,822,187 | 7/1974 | Du Chaffaut | 195/28 R |
| 3,915,802 | 10/1975 | Kominek | 195/115 X |
| 3,926,737 | 12/1975 | Wilson et al. | 195/108 |

OTHER PUBLICATIONS

Bu'Lock "Secondary Metabolism of Microorganisms", *Industrial Aspects of Biochemistry*, vol. 30, Spencer ed., North-Holland Co., Amsterdam, (1974), pp. 335-346.

*Primary Examiner*—Thomas G. Wiseman
*Attorney, Agent, or Firm*—Kenway & Jenney

[57] ABSTRACT

A fermentation vessel is used to grow a cell mass and maintain it in a maintenance energy state. In this state the mass of the cell material is maintained substantially constant, and fresh medium containing an energy source is introduced to the vessel at a rate sufficient to sustain cell viability but insufficient to support growth of the cell mass. Fluid with suspended cells is pumped from the vessel to a separator which separates a fraction of the fluid from the cells and discharges the fraction, the unfiltered portion of the fluid and substantially all of the cells being returned to the vessel, the discharged fraction containing useful secondary metabolites.

14 Claims, 1 Drawing Figure

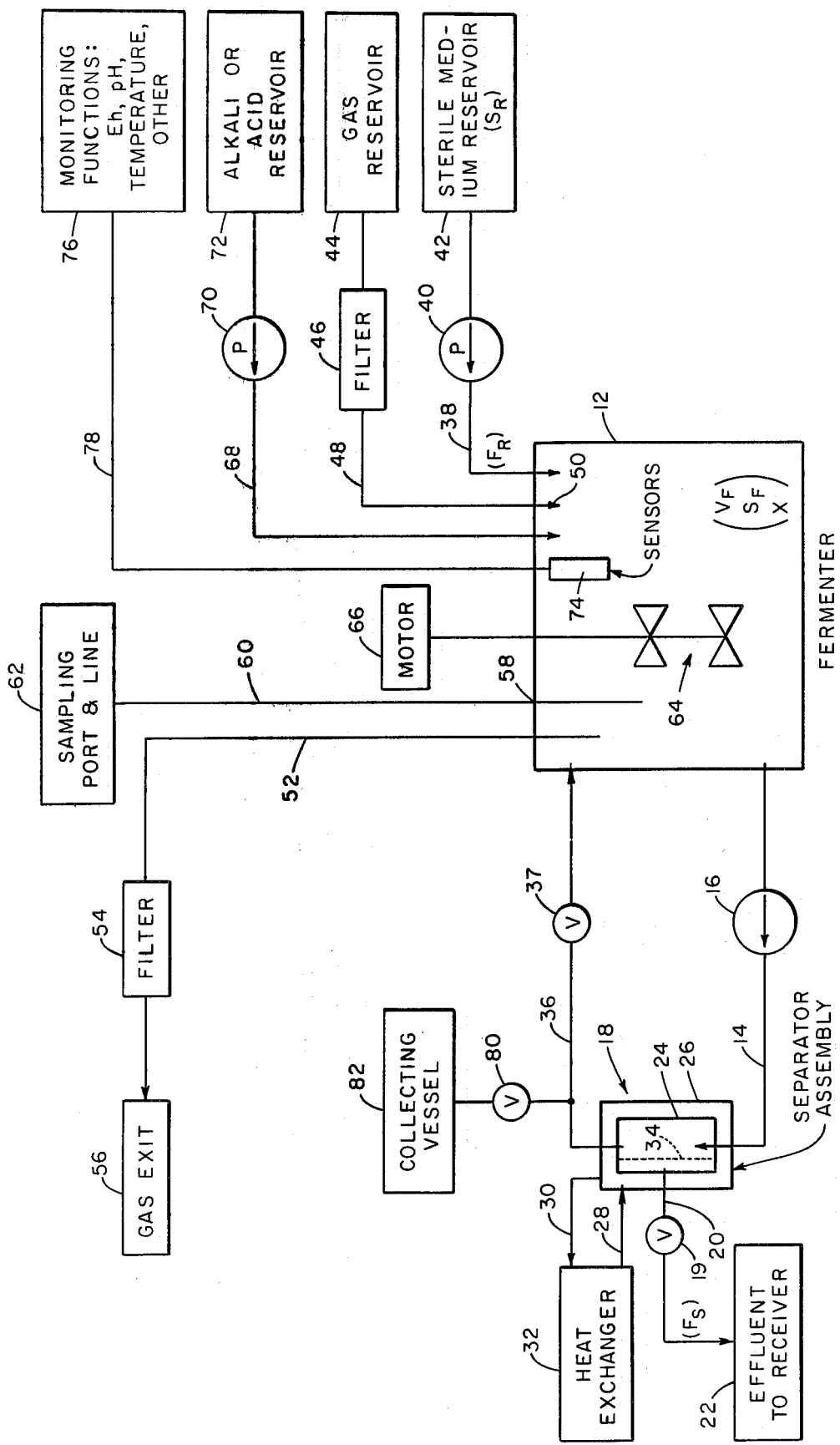

METHOD AND APPARATUS FOR THE PRODUCTION OF SECONDARY METABOLITES BY THE MAINTENANCE-STATE CULTIVATION OF MICROORGANISMS

BACKGROUND OF THE INVENTION

The invention described herein was made in the course of work under a grant or award from the Department of the Army.

This invention relates generally to the cultivation of microorganisms, and more particularly to techniques for attaining and maintaining a state of cell viability corresponding to maximum efficiency of conversion of introduced medium to commercially desirable effluent.

The principal object of the invention is to provide a system which has the capability of placing and maintaining a culture of single cell microorganisms in a condition in which certain features or characteristics of the culture having practical and commercial utility are maximized, and certain desirable microbial products can be continuously obtained in a partially purified form.

It has been known for some time that when microorganisms are grown in batch culture, that is, in a closed system in which no further nutrients are added, and no growth products (other than certain gases such as $CO_2$) are removed, once the seeding charge of microorganisms is introduced, a typical sequence of growth stages is observed: (1) a lag phase of slow or linear growth; (2) an exponential phase in which the change of microbial mass in the system is described by $$X = X_o e^{ut} \qquad \text{Eq. (1)}$$

where
- $X$ = grams of dry weight of cell material per ml in the batch, at the time of observation
- $X_o$ = grams of dry weight of cell material per ml in the batch, at a previous time of observation
- $u$ = the specific growth rate of the organism
- $t$ = the time interval between observations;

(3) a stationary phase of indeterminate length in which there is no further net increase in microbial mass; and (4) a declining or death phase in which the microorganisms die.

It has been further known that many compounds of commercial interest (sometimes called secondary metabolites) such as enzymes, toxins, antibiotics or various large complex organic molecules are produced at a maximum rate during the transition from the exponential phase to the stationary phase or in the stationary phase. (Weinberg, E.D. 1971. Secondary metabolism: raison d'être. Persp. in Biol. Med. 14:565–577). It is currently believed that this occurs as a result of inherent biological properties of microbial cells, particularly the property of derepression of genetic information which is partly under the control of the nucleotide 3'-5' cyclic adenosine monophosphate, whose cellular concentration is at a maximum in this period.

A number of systems have been proposed to extend this transition interval, or the stationary phase itself, to realize an increased production of secondary metabolites, or an increased capability for bringing about certain metabolic transformations, e.g., steroid transformations or decomposition of waste molecules in waste treatment. U.S. Pat. No. 3,015,612 issued Jan. 2, 1962 to Stanley J. Pirt, et. al. describes such a system involving two sequentially linked fermenters in which the metabolic condition of the organisms in the second fermenter has some of the features of the condition of stationary phase organisms produced in batch culture. Pirt's system, however, is an open system: fresh nutrients continuously enter the system and cells and product are continuously removed.

It has also been known for some time that microorganisms cannot use all of the energy available to them for growth processes, but must use part of that energy for maintenance processes necessary to sustaining cell viability, but not producing a net increase in cell mass. This fraction of the energy available to the cells has been called maintenance energy. (Pirt, S. J. 1965. The maintenance energy of bacteria in growing cultures. (Proc. Roy. Soc. (London) Ser. B. Biol. Sci. 163(991): 224–231).

The present invention comprises a method and apparatus by which a culture of single celled organisms is brought to a condition believed to be novel, called the maintenance state, in which greater than 90% of the energy available to the cell must be utilized for maintenance processes. In the practice of this invention many useful and commercially desirable features associated with late exponential and stationary phases in batch culture are attainable with this novel state. Further, the apparatus brings about an immediate and useful fractionation of the desired end products from other parts of the system.

BRIEF DESCRIPTION OF THE DRAWING

The drawing is a schematic representation of the preferred form of apparatus according to the invention, and includes elements useful in performing certain variants of the process as hereinafter more fully described.

DETAILED DESCRIPTION

The preferred system comprises a fermentation vessel 12 of volume $V_F$ which is completely enclosed and sealed from its external environment except for the indicated access and exit lines. The fermenter is attached through a line 14 containing a pump 16 of appropriate and variable pumping capacity to a separator section 18. The function of the section 18 is to continuously separate from the cell mass a part of the fluid in which the cells are suspended so that the separated fluid exits from the separator assembly through a valve 19 and a line 20 to a receiver 22 at a flow rate $F_S$. This separated fluid will contain the desired products immediately separated from the cell mass.

By alternative arrangements of the separation device differing degrees of fractionation can be achieved. For example, by using filters of known pore sizes, molecules of differing dimensions can be retained or immediately further fractionated and concentrated; or by imposition of an electrical field across the separator, effluent molecules of different charges would be fractionated and concentrated. Similarly, ion exchange materials, bound molecules with particular affinities for the desired product, heat as in distillation, counterflow of organic extractants or precipitants can be incorporated in the separator function and immediately applied to fractionation and concentration of desired materials in the product stream in the line 20. Alternatively, if the system is being used to procure the degradation, decomposition, or transformation of toxic, annoying, or otherwise undesirable materials in the input medium by action of the organisms in the fermenter, then an effluent with the undesired component either reduced in concentration, or eliminated, is immediately obtained in the line 20 from the separator function.

In the illustrated embodiment, the separator section 18 comprises an assembly having a canister 24 and a surrounding jacket 26. The jacket is connected by lines 28 and 30 to a heat exchanger 32 further described below. The canister is completely sealed from the surrounding space within the jacket. Mounted within the canister is a filter 34. The pump 16 pumps fluid containing suspended organisms along one side of the filter. The filter is a circular sheet of porous polycarbonate, 150 mm in diameter, 10 microns thick, containing $3 \times 10^8$ pores per cm$^2$, each 0.2 microns in diameter. The canister is formed of stainless steel and sealed along its entire periphery. The entire separator section is closed so as to protect the system from contamination. By adjustment of the pump speed or the valve 19 or a combination of these, a positive pressure is maintained across the filter, varying from 5 to 30 psi as required to obtain a filtrate rate $F_S$ equal to the medium input rate to the fermenter $F_R$, hereinafter described. The polycarbonate sheet is contained and sealed along its entire periphery in the stainless steel canister, effectively separating retentate and filtrate sides of the separator and preserving the aseptic condition of the apparatus.

Other configurations of the separator section will be recognized by those skilled in the art as acceptable alternatives to the embodiment shown. For example, the filter sheet 34 could be embodied in a wall of the fermenter, rendering it unnecessary to remove any cells therefrom. In this case the pressure differential across the filter can be controlled by altering the pressure within the fermenter.

The separated, and partially concentrated cell mass is completely and continuously returned to the fermenter through a line 36 and a valve 37 which can also be adjusted to control the pressure differential across the sheet 34. This is necessary to obtain the maintenance state in the fermenter, and to sustain it. In this way, the process differs from previously described systems in which some part of the cell mass is continuously and permanently withdrawn from the fermenter. However, under certain specified conditions of operation described below, part of the cell mass can be withdrawn, if desired, without perturbing the maintenance state.

Medium is continuously introduced into the fermenter through a line 38 by the action of a pump 40 of appropriate and variable pumping capacity, at a flow rate $F_R$. The pump 40 is connected with a sterile medium reservoir 42. It will usually be desirable that the medium in the reservoir be made sterile prior to introduction to the fermenter, which may be achieved by filtration, heating, irradiation, or in any other manner commonly used to effect sterilization and appropriate to the circumstances.

The medium in the reservoir, also called substrate, comprises a mixture including all nutrients necessary to growth of the culture. One or more of these nutrients, for example glucose, comprise an energy source which is present on the reservoir 42 in a concentration $S_R$. In the preferred practice of this invention a predetermined volume of this medium is initially placed in the fermenter and seeded with a charge of the desired organism or mixture of organisms previously grown in a medium of the same formulation. Then, as the cell mass begins to grow the pump 40 is turned on to produce a steady flow of the medium into the fermenter at the volume rate $F_R$. When the medium, the flow rate and other parameters satisfy the conditions hereinafter described, the cell mass will grow to a certain ultimate population and will not increase thereafter but will remain constant in the maintenance state. These conditions are such that there will be insufficient energy source in the fermenter to supply more than the maintenance energy required for this ultimate mass, although all other nutrients necessary for further growth are present. It is critical to the operation that the medium be so constituted that all nutrients necessary to growth of the culture in the fermenter, except the energy source, are present when the ultimate microbial population is achieved. The energy source has an influent concentration $S_R$, so that the concentration $S_R$ is the sole factor limiting growth in the fermenter initially.

When the maintenance state is achieved, as described below, the product $S_R \times F_R$ (also termed the mass transfer rate) must remain constant for as long as it is desired to keep the culture in this state, but the concentration of other components of the medium, except oxygen, may be altered once the maintenance state is approximated providing that this alteration does not affect the viability of the cells in the fermenter.

A gas reservoir 44 is connected through a filter 46 to a line 48 leading to a distributive head or heads 50, commonly called spargers, within the reservoir. An input of gas or gases to the fermenter is essential for the culture of some types of organisms. For aerobic organisms, the gas input will be either air, oxygen-enriched air, or oxygen. Anaerobic organisms may be cultured either without gas introduction, or with introduction of an appropriate gas such as nitrogen or carbon dioxide, free of oxygen and oxides, and similarly directed into or onto the medium in the fermenter. Other gases or gas mixtures may be used as desired, but all will usually be rendered sterile by heating, irradiation, or filtration prior to introduction into the fermenter.

A line 52, a filter 54 and gas exit means 56 are provided to remove either gases introduced into the fermenter, or gases produced by the metabolism of the culture. Filtration, or heating or irradiation means (not shown) in the line 52 prevent access of undesired organisms to the fermenter, or egress of airborne organisms from the fermenter.

The fermenter has a sampling port 58 and line 60 through which samples may be periodically removed aseptically from the fermenter to sampling port and line means 62. The seeding charge of organisms, or other materials are introduced directly into the fermenter through the line 60.

The apparatus has a mixing device 64, power driven by a motor 66. The device 64 has seals or other means to prevent material from entering or leaving the fermenter along the drive coupling.

The apparatus has a line 68 containing a suitable variable speed pump 70 connected to a reservoir 72 of acid or alkali. By this means these substances may be sterilely added to the fermenter at a controlled rate.

The apparatus is equipped with sensors 74 connected to a monitoring functions unit 76 by leads 78. The sensors are suitable for monitoring the pH, Eh and temperature of the fermenter contents. It may be further desired to provide sensors for monitoring dissolved oxygen, cell density, conductance, osmotic pressure, viscosity or a variety of ionized and nonionized solutes, such as ammonium or sucrose. The pH sensor may be used to control the rate at which acid or alkali is added to the fermenter, through any of several available transducing and control devices, and so maintain a constant pH in the fermenter. Similarly, the dissolved oxygen concentration in the fermenter may be regulated by an appropriate sensor acting through a transducer and variable setting valves to control the rate of oxygen admission to the fermenter. And in a like manner, a number of other concentrations or quantities pertaining in the fermenter may be stabilized or varied.

The illustrated embodiment of the separator section 18 is equipped for heat exchange concurrently with its primary function, so that the temperature of the fermenter may be kept constant or varied. Alternatively, a heat exchange system may be incorporated into the fermenter; or the entire fermenter may be wholly or partially immersed in a heat exchange medium to attain the same effects.

The entire system is preferably sterilizable when desired by heat or gaseous or fluid sterilants such as formaldehyde, chlorine, or peracetic acid.

In operation, after the system has been sterilized the fermenter is filled as described above to a volume $V_F$ with sterile medium, and seeded with the desired organism. The maintenance state will then be achieved when the system is operated in the following manner.

Temperature and pH are controlled at constant values appropriate to optimum operation of the system. If the culture is aerobic and oxygen is being introduced into the fermenter, the rate of its introduction will be fixed at an appropriate level to insure as complete as possible oxidation of the energy substrate in the maintenance state. If the culture is anaerobic, the Eh, that is, the redox or reduction-oxidation potential as measured between suitable electrodes in the fermenter, may be poised at some desired level by the addition of a reducing compound such as dithiothreitol, or by a continuous sweep with nitrogen or carbon dioxide which is oxygen and oxide free.

The fermenter contents are kept homogenous by operation of the mixing device 64 and fresh medium is pumped continuously into the fermenter at a constant rate $F_R$. The value of this rate will be chosen such that the product $F_R \times S_R$ will produce the desired ultimate cell mass in the fermenter in constraint with equation (3) given below. The separator is set in operation to produce an effluent flow $F_S = F_R$, and to return a volume to the fermenter at a rate such that a volume equal to $V_F$ will be returned to the fermenter usually in a period about 1/5 the mass doubling time now observed in the fermenter, but which may be varied somewhat provided satisfactory attainment and retention of the maintenance state is achieved.

After the fermenter is thus set in operation, the mass of cell material will change in the following predictable ways. It will increase initially at an exponential rate until about 10% of the maintenance state mass, $X_M$, is achieved. Its rate of increase will then decrease as the concentration $S_F$ of the energy source in the fermenter, becomes very low and approaches 0. For a relatively short interval thereafter, the cell mass will be determined approximately by the expression:

$$X = [C][F_R][S_R][t] + X_E \qquad \text{Eq. (2)}$$

where
$X$ = grams of dry weight of cell material per ml fermenter fluid
$C$ = a proportionality constant
$t$ = time of observation
$X_E$ = grams of dry weight of cell material per ml fermenter fluid at the end of the exponential phase (equation 1) and
$S_R$ and $F_R$ are as previously defined.

The rate of change of X will continue to fall at a rate dependent on the type of organism used, asymptotically approaching 0 as X approaches within 90% of $X_M$. At this point the culture is effectively in the maintenance state, and mass transfer in the system is effectively described by:

$$X_M = \frac{F_R}{V_F} \left[ \frac{S_R - (S_F + S_A)}{M_C} \right] \qquad \text{Equation (3)}$$

where
$X_M$ = grams of dry weight of cell material per ml fermenter fluid, in the maintenance state
$F_R$ = ml of fresh medium entering the fermenter per hour
$V_F$ = volume of fermenter and retentate side of the separator assembly in ml
$S_R$ = moles of the energy source per ml fresh medium
$S_F$ = moles of the energy source per ml fermenter fluid unavailable for dissimilation or assimilation which is a function of the state of growth and of the particular organism, and approaches zero as the population nears $X_M$
$S_A$ = moles of the energy source assimilated into cell stuff per ml of fermenter fluid
$M_C$ = the maintenance coefficient-moles of energy substrate consumed for maintenance processes per gram cell dry weight per hour Maximum derepressibility of the culture is observed and the greatest possible percent conversion of substrate to excreted and secreted product will obtain. The concentration of these products in the fermenter and in the effluent line from the separator assembly will be related to influent substrate in the steady maintenance state by:

$$P_F = [S_R] k_{SP} \qquad \text{Eq. (4)}$$

where
$P_F$ = mass of product per ml fermenter fluid,
$k_{SP}$ = factor for conversion of substrate to product = unit mass of product formed per unit mass of energy source (also termed substrate) metabolized, and
$S_R$ has the meaning previously assigned.

It is characteristic of the system that, as long as $F_R$ and $F_S$ are kept equal to each other, they can be varied without affecting $P_F$, although $X_M$ will change to the value predicted by equation (3), and a greater or lesser amount of substrate will be metabolized per unit time as $F_R$ and $F_S$ are increased or decreased.

These characteristics of the system provide a flexibility of great utility since they permit it to be used in circumstances where either very low $P_F$ and high $F_R$ values are desired as in treatment of fluid wastes, or conversely where high $P_F$ and low $F_R$ values are desired as in production of a useful compound such as an enzyme or an organic solvent, or in producing any intermediate combinations of $P_F$ and $F_R$, while keeping the reactor volume of the system, i.e., the fermenter and its attachments, constant and at a minimum size.

Cell mass can be withdrawn from the fermenter without perturbing the maintenance state, providing the product $S_R \times F_R$ is concurrently adjusted, using equation (3), to the level necessary to maintain the reduced cell population. The removed cell mass cannot be regained in the fermenter, however, without permitting growth to take place. The following are examples of particular applications of the system, but it will be understood that they are given only by way of illustration and not in a limitative sense.

EXAMPLE 1

The bacterium *Escherichia coli* B (ATCC) was grown for 18 hours at 30° C. under anaerobic conditions in a sterile medium of the following composition:

| | |
|---|---|
| glucose | 2.5 grams |
| $K_2HOP_4$ | 7.0 grams |
| $KH_2PO_4$ | 3.0 grams |
| $(NH_4)_2SO_4$ | 1.0 grams |
| Na Citrate . 2 $H_2O$ | 0.5 grams |
| $MgSO_4$ . 7 $H_2O$ | 0.1 gram |
| distilled water | 1000 milliliters |

Thirty ml of this culture were used to seed the sterile fermenter containing a charge of 450 ml of the same sterile medium or substrate. The fermenter system and the reservoirs of sterile medium were maintained at an Eh or reduction-oxidation potential of −200 mv by continuous sweep with nitrogen rendered oxygen and oxide free by passage through a solution of alkaline 20% pyrogallol. The pH of the fermenter contents was maintained at 7.0 by continuous addition of sterile 2 N NaOH and the temperature at 30° C. The value of $F_S$ and $F_R$ were maintained constant at all times.

At 70 hours, $X_M$ was 2.5 mg per ml. For the following 30 hours $X_M$ remained nearly constant. The following compounds were found in the effluent line 20 during this interval at the concentrations given below:

| 1. | Products of glucose dissimilation | |
|---|---|---|
| | Lactic acid | 3.0 $\mu$ moles/ml |
| | succinic acid | 8.9 $\mu$ moles/ml |
| | acetic acid | 6.0 $\mu$ moles/ml |
| | formic acid | 12.0 $\mu$ moles/ml |
| | ethanol | 6.0 $\mu$ moles/ml |
| 2. | Products of glucose assimilation | |
| | deoxyribonucleotides | 56 $\mu$g/ml |
| | ribonucleotides | 20 $\mu$g/ml |
| | proteins | 36 $\mu$g/ml |
| | lipopolysaccharide | 20 $\mu$g/ml |

The products of glucose assimilation found in the effluent illustrate how the system may be used to produce, in addition to the compounds shown, vitamins, antibiotics, transformed steroids, amino acids, sugars, sugar alcohols, lipids and lipoidal materials and various combinations and polymers of these substances through placing an organism secreting these substances in the system in the maintenance state.

The sum of the grams of carbon in all the products divided by the grams of carbon in the substrate indicates an analytical recovery of 104% of the substrate carbon in the products.

Throughout the interval of the maintenance state, the cellular population retained greater than 91% viability.

EXAMPLE 2

In a second application the yeast *Saccharomyces cereviseae*, strain FH4C, which constitutively produces and secretes the enzyme invertase, was grown for 24 hours at 25° C. under unaerobic conditions in a medium of the following composition:

| | |
|---|---|
| glucose | 4.5 grams |
| $[NH_4]_2PO_4$ | 2.0 grams |
| KCl | 1.15 grams |
| $MgSO_4$ . 7 $H_2O$ | 0.65 grams |
| $MnSO_4$ . 1 $H_2O$ | 0.045 grams |
| $FeSO_4$ . 7 $H_2O$ | 0.068 grams |
| yeast extract | 0.05 grams |
| distilled water | 1000 milliliters |

Ten ml of this culture were added aseptically to a fermenter volume $V_F$ of 450 ml of the same medium. The system was anaerobic and was maintained so as described in Example 1. The pH was maintained at 6.0 and sterile medium of the same composition was continuously added to the fermenter at a rate $F_R$ of 120 ml per hour and withdrawn from the separator function at the same rate. After 90 hours at 25° C., $X_M$ was 1.54 mg dry weight per ml and remained at or very near this value thereafter. During the next 30 hours of observation the following compounds were found in the effluent line 20 at the concentrations given.

| 1. | Products of glucose dissimilation | |
|---|---|---|
| | ethanol | 40 $\mu$ moles per ml |
| | glycerol | 4 $\mu$ moles per ml |
| 2. | Products of glucose assimilation | |
| | invertase | 370 $\mu$g of protein per ml |

In this example (2), the yield of ethanol and glycerol can be increased, if desired, without greatly increasing $X_M$, the maintenance state cell mass in the fermenter, by increasing the substrate concentration $S_R$ and the maintenance coefficient $M_C$. The latter can be accomplished by stressing the cells during the fermentation, as by lowering the pH to 3.0, or increasing the temperature to 38°–40° C. Other physiological stresses might also be used and, in general, the biodegradative capacity of the system for the same cell mass in the maintenance state can be increased in this way.

EXAMPLE 3

A third example describes production of cell mass from substrate with maximum efficiency using the maintenance state. The yeast strain *Saccharomyces cereviseae* S90 was grown for 25 hours at 25° C. in 50 ml of a medium of the same composition as described previously in Example 2 in a 250 ml, cotton stoppered Erlenmeyer flask continuously shaken at 200 RPM. Ten ml of this culture was used to seed 450 ml of sterile medium $V_F$ of the same composition in the fermenter. The same sterile medium was pumped to the fermenter at a rate $F_R$ of 120 ml per hour and the separated effluent withdrawn at the same rate. When analysis indicated that the glucose concentration in the fermenter was near 0, filter sterilized oxygen was introduced into the fermenter through a glass sparger 50 at rates sufficient to maintain a dissolved oxygen concentration of 50% of saturation. When a dry weight $X_M$ of 20.3 milligrams of yeast cells per ml was achieved in the fermenter, the effluent line contained less than 1% of the compounds described in Example 2. The cell concentrate flowing in the return line from the separator to the fermenter was diverted through a sterile valve 80 into a collecting vessel 82; $F_S$ was increased to 300 ml per hour, while $F_R$ was reduced to 0, until the fermenter volume, $V_F$, was reduced to 150 ml, at which time diversion of cell concentrate to the vessel 82 was terminated.

$F_R$ was then returned to 120 ml per hour while $F_S$ was kept at 0 until $V_M$ had returned to 450, then $F_S$, was returned to 120 ml hour$^{-1}$. The withdrawal process was then repeated. From each collected cell concentrate, 600 mg of dried yeast were collected representing a 61% assimilation of substrate carbon.

This example (3) illustrates, first, that the system can be used to produce cell mass from a carbonaceous energy source with maximum efficiency, and second, that it can function to completely metabolize a substrate with maximum efficiency, which would be a desirable feature of its use as a waste treatment system.

A further possible application would be to culture a nitrogen-fixing organism, for instance *Bacillus polymyxa*, in a medium containing a carbonaceous energy source and all other nutrients necessary to achieve the maintenance state excepting that nitrogen be present only in the gaseous form, $N_2$. When the maintenance state is achieved, the effluent line will contain useful dissimilation products, such as 2:3-butanediol, and a variety of proteins, such as glucoamylase, containing nitrogen reduced and bound in organic form, so that the system effectively operates to fix atmospheric nitrogen. Other organisms, such as anaerobic Clostridium species, or aerobic organisms Azotobacter species, which fix atmospheric nitrogen might also be used.

We claim:

1. A method of growing and maintaining a culture of microorganisms in a state wherein greater than 90 percent of the energy source available to the culture is utilized for maintenance energy, comprising the steps of providing in a closed system comprising a vessel connected to a filtration means in a manner which allows the continuous withdrawal of filtrate free of cells from the system, an initial fluid medium seeded with cells of selected microorganisms, the medium containing nutrient material comprising a source of maintenance energy for the cells, and initially cultivating the cells causing the mass of said cells to increase and the concentration of said source to decrease, introducing additional medium containing said source at a volume rate $F_R$ into the vessel as said mass is increasing wherein the volume rate is controlled so that the product of the rate $F_R$ and the energy substrate concentration $S_R$ of said source is constant, and further cultivating the cells until the rate of increase of said mass is progressively reduced to a minimum and a concentration of cells, $X_m$, is obtained which satisfies the following relationship $$X_m = \frac{F_R}{V_F}\left[\frac{S_R - (S_F + S_A)}{M_c}\right]$$

thereby achieving said state, wherein $X_m$ is the cell mass per unit fluid volume in said system, $V_F$ is the fluid volume in said system, $S_F$ is the concentration of said source in said system, $S_A$ is the amount of said source assimilated into the cells per unit fluid volume in said system, and $M_c$ is a coefficient relating the rate of utilization of the energy source for maintenance energy to the cell mass, and wherein $S_F$ is permitted to decrease substantially to zero upon the cells reaching said state, filtering a portion of the medium in the system and products of metabolism therein from the cells, said portion being free of cells, and transferring said portion at a rate $F_S$ to a receiver.

2. The method according to claim 1, in which the introduction of additional medium and the transfer of said portion to the receiver proceed at equal volume rates.

3. The method according to claim 1, in which said initial medium combined with said additional medium introduced into the vessel contain said source and all other ingredients required for growth of the cells, the ratios of energy source to said other ingredients being such that the depletion of the energy source and not of said other ingredients in the vessel limits the growth of the cell mass.

4. The method according to claim 3, in which the ratio of the energy source to said other ingredients in said initial quantity of medium equals the corresponding ratio in said additional medium.

5. The method according to claim 1, in which said filtering is accomplished by passing the withdrawn medium adjacent to a porous barrier having pores of a size permitting passage of solvents and solutes, but not of cells.

6. The method according to claim 5, in which a pressure differential is maintained across said barrier sufficient to withdraw said portion at said rate $F_S$.

7. The method according to claim 1, including controlled elimination of toxic substances in the vessel to prevent their accumulation above a predetermined concentration.

8. The method according to claim 1, including maintenance of the temperature of the cell mass within predetermined constant limits.

9. The method according to claim 1, including maintenance of the pH of the contents of the vessel within predetermined constant limits.

10. The method according to claim 1, including maintenance of the level of dissolved oxygen in the contents of the vessel within predetermined constant limits.

11. The method according to claim 1, including maintenance of the reduction-oxidation potential in the contents of the vessel within predetermined constant limits.

12. The method according to claim 1, including controlled elimination from the vessel of gases produced by metabolism of the cells.

13. The method according to claim 1, in which said closed system and all materials introduced into it except the seed cells are sterilized and effectively isolated from the environment.

14. A method of growing and maintaining a culture of microorganisms in a state wherein greater than 90 percent of the energy source available to the culture is utilized for maintenance energy, comprising the steps of providing in a closed system comprising a vessel connected to a filtration means in a manner which allows the continuous withdrawal of filtrate free of cells from the system, an initial fluid medium seeded with cells of selected microorganisms, the medium containing nutrient material comprising a source of maintenance energy for the cells, and initially cultivating the cells causing the mass of said cells to increase and the concentration of said source to decrease, introducing an additional medium containing said source at a volume rate $F_R$ into the vessel as said mass is increasing, wherein the volume rate is controlled so that the product of the rate $F_R$ and the energy substrate concentration $S_R$ of said source is constant, and further cultivating the cells until the rate of increase of said mass is progressively reduced to a minimum and a concentration of cells, $X_m$, is obtained which satisfies the following relationship $$X_m = \frac{F_R}{V_F} \left[ \frac{S_R - (S_F + S_A)}{M_c} \right]$$

thereby achieving said state, wherein $X_m$ is the cell mass per unit fluid volume in said system, $V_F$ is the fluid volume in said system, $S_F$ is the concentration of said source in said system, $S_A$ is the amount of said source assimilated into the cells per unit fluid volume in said system, and $M_c$ is a coefficient relating the rate of utilization of the energy source for maintenance energy to the cell mass, and wherein $S_F$ is permitted to decrease substantially to zero upon the cells reaching said state, remaining to a collector a fraction of the cells and medium and reducing said product of the rate $F_R$ and the energy substrate concentration $S_R$ until the contents in said system reach a desired fraction of the quantity present before said drawing off, and terminating said removal when the desired level is reached and increasing said product until the contents of said system are increased to a $F_R S_R$ desired value, and thereafter maintaining said product $F_R S_R$ constant and permitting the cell mass to increase until the value of $S_F$ is again decreased substantially to zero and the cell mass again reaches said state.

* * * * *

UNITED STATES PATENT AND TRADEMARK OFFICE
CERTIFICATE OF CORRECTION

PATENT NO. : 4,167,450
DATED : September 11, 1979
INVENTOR(S) : William R. Chesbro, et al It is certified that error appears in the above-identified patent and that said Letters Patent are hereby corrected as shown below:

Column 9, (claim 1), line 46, after "increasing" insert --,--.

Column 12, (claim 14), line 6, "remaining" should read --removing--; line 10, "drawing off" should read --removal--; line 12, after "product" insert --$F_R S_R$--; line 13, cancel "$F_R S_R$".

Signed and Sealed this

First Day of January 1980

[SEAL]

Attest:

SIDNEY A. DIAMOND

Attesting Officer

Commissioner of Patents and Trademarks